(12) United States Patent
Kim et al.

(10) Patent No.: US 11,369,313 B2
(45) Date of Patent: Jun. 28, 2022

(54) PATCH-TYPE SENSOR MODULE

(71) Applicant: AMOLIFESCIENCE CO., LTD., Seoul (KR)

(72) Inventors: Beom Jin Kim, Bucheon-si (KR); Yun Hee Chung, Seoul (KR); Ji Hyun Lee, Incheon (KR); Kyung Hyun Ryu, Seoul (KR)

(73) Assignee: Amolifescience Co., Ltd., Seoul (KR)

( * ) Notice: Subject to any disclaimer, the term of this patent is extended or adjusted under 35 U.S.C. 154(b) by 112 days.

(21) Appl. No.: 16/468,435

(22) PCT Filed: Dec. 12, 2017

(86) PCT No.: PCT/KR2017/014522
§ 371 (c)(1),
(2) Date: Jun. 11, 2019

(87) PCT Pub. No.: WO2018/110932
PCT Pub. Date: Jun. 21, 2018

(65) Prior Publication Data
US 2019/0328327 A1  Oct. 31, 2019

(30) Foreign Application Priority Data

Dec. 13, 2016 (KR) .................. 10-2016-0169609
Jun. 13, 2017 (KR) .................. 10-2017-0074077
Jun. 13, 2017 (KR) .................. 10-2017-0074184

(51) Int. Cl.
*A61B 5/00* (2006.01)
*H04W 4/80* (2018.01)
(Continued)

(52) U.S. Cl.
CPC ............ *A61B 5/6833* (2013.01); *A61B 5/002* (2013.01); *A61B 5/01* (2013.01); *A61B 5/02055* (2013.01);
(Continued)

(58) Field of Classification Search
CPC ....... A61B 5/002; A61B 5/01; A61B 5/02055; A61B 5/6833; A61B 5/0008;
(Continued)

(56) References Cited

U.S. PATENT DOCUMENTS 6,136,327 A * 10/2000 Gupta ................... A61N 1/30
424/400
9,311,686 B2   4/2016 Roush et al.
(Continued)

FOREIGN PATENT DOCUMENTS

KR       100915320 B1    9/2009
KR       20100094256  *  8/2010 ............. A61K 47/34
(Continued)

OTHER PUBLICATIONS

Machine translation of KR20100094256. (Year: 2020).*
Ndian Office Action cited in Application No. 201927021941, dated May 7, 2021, 6 pages.

*Primary Examiner* — Carl H Layno
*Assistant Examiner* — Aya Ziad Bakkar
(74) *Attorney, Agent, or Firm* — Rothwell, Figg, Ersnt & Manbeck, P.C.

(57) ABSTRACT

A patch-type sensor module is provided. A patch-type sensor module according to one embodiment of the present invention comprises: a power supply unit electrically connected with a flexible circuit board; a sensing unit which is mounted on the flexible circuit board and includes a temperature sensor for measuring a user's body temperature; a communication unit which allows power to be supplied using a wake-up function, wherein a pairing with an external communication module is concurrently established when power is supplied, and information measured through the sensing unit is then transmitted to the external communication module; a control unit for controlling operations of the power supply unit, the sensing unit, and the communication (Continued)

unit; and a protection member for preventing the flexible circuit board, the power supply unit, the sensing unit, the communication unit, and the control unit from being exposed to the outside.

17 Claims, 10 Drawing Sheets

(51) Int. Cl.

| | |
|---|---|
| *A61B 5/01* | (2006.01) |
| *A61B 5/0205* | (2006.01) |
| *H04B 5/00* | (2006.01) |
| *H05K 1/18* | (2006.01) |
| *H04W 12/47* | (2021.01) |
| *A61B 5/259* | (2021.01) |
| *A61B 5/282* | (2021.01) |
| *G01J 1/42* | (2006.01) |
| *H04W 12/06* | (2021.01) |
| *H05K 5/02* | (2006.01) |
| *H05K 5/06* | (2006.01) |
| *G01K 13/20* | (2021.01) |

(52) U.S. Cl.
CPC .............. *G01J 1/429* (2013.01); *G01K 13/20* (2021.01); *H04B 5/0037* (2013.01); *H04W 4/80* (2018.02); *H04W 12/06* (2013.01); *H04W 12/47* (2021.01); *H05K 1/189* (2013.01); *H05K 5/0247* (2013.01); *H05K 5/065* (2013.01); *A61B 5/0006* (2013.01); *A61B 5/0008* (2013.01); *A61B 5/259* (2021.01); *A61B 5/282* (2021.01); *A61B 2560/0214* (2013.01); *A61B 2560/0412* (2013.01); *A61B 2562/029* (2013.01); *A61B 2562/164* (2013.01); *A61B 2562/18* (2013.01); *H05K 2201/10037* (2013.01); *H05K 2201/10098* (2013.01); *H05K 2201/10151* (2013.01)

(58) Field of Classification Search
CPC ............ A61B 2562/029; A61B 5/0006; G01K 13/002; H05K 2201/10037; H05K 1/189; H04W 12/06
See application file for complete search history.

(56) References Cited

U.S. PATENT DOCUMENTS

| | | | |
|---|---|---|---|
| 9,433,380 | B1* | 9/2016 | Bishay ................ A61B 5/6833 |
| 2014/0121557 | A1* | 5/2014 | Gannon ................ G01K 1/024 |
| | | | 600/549 |
| 2015/0035680 | A1* | 2/2015 | Li ............................ G01K 1/14 |
| | | | 340/584 |

FOREIGN PATENT DOCUMENTS

| | | |
|---|---|---|
| KR | 101080203 B1 | 11/2011 |
| KR | 20120078202 A | 7/2012 |
| KR | 20150066560 A | 6/2015 |
| KR | 20150083321 A | 7/2015 |

\* cited by examiner

PATCH-TYPE SENSOR MODULE

CROSS REFERENCE TO RELATED APPLICATION

This application is a 35 U.S.C. 371 National Phase Entry Application from PCT/KR2017/014522, filed Dec. 12, 2017, which claims the benefit of Korean Patent Application Nos. 10-2016-0169609 filed on Dec. 13, 2016, 10-2017-0074077 and 10-2017-0074184 filed Jun. 13, 2017, the disclosures of which are incorporated herein in their entireties by reference.

TECHNICAL FIELD

The present invention relates to a patch-type sensor module, and more particularly, to a patch-type sensor module which is capable of acquiring biometric data of a user.

BACKGROUND ART

Generally, in measuring of a body temperature and a heartbeat of a body, thermometers of a contact type and a non-contact type may be used. Examples of general thermometers include a mercury thermometer, an alcohol thermometer, an infrared sensor thermometer, and the like.

These thermometers may acquire information on the body temperature after waiting for a certain period of time in a state of being worn on or being in contact with the body.

Accordingly, since people around babies, infants, and patients with mobility difficulties should help them to maintain a state of wearing a thermometer on their bodies, there is a problem of measuring a body temperature being cumbersome.

Further, since the conventional thermometer is in contact with a body of a target person for a certain period of time and then is separated from the body of the target person so that a body temperature is checked, checking the body temperature in real time or periodically is inconvenient.

In addition, since the conventional thermometer is able to measure only the body temperature, there is a problem in that a separate sensor or equipment is inevitably required so as to acquire other information from the target person.

DISCLOSURE

Technical Problem

The present invention is directed to providing a patch-type sensor module which is capable of being easily attached to a user's body and monitoring biometric data including user's body temperature information in real time.

Further, the present invention is directed to providing a patch-type sensor module which is capable of recharging a battery.

Technical Solution

One aspect of the present invention provides a patch-type sensor module including a power supply unit electrically connected to a flexible circuit board, a sensing unit mounted on the flexible circuit board and including a temperature sensor configured to measure a user's body temperature, a communication unit for allowing power to be supplied using a wake-up function and for transmitting information measured by the sensing unit to the external communication module through a pairing with an external communication module when power is supplied, a control unit configured to control driving of the power supply unit, the sensing unit, and the communication unit, and a protection member configured to prevent the flexible circuit board, the power supply unit, the sensing unit, the communication unit, and the control unit from being exposed to the outside.

The sensing unit may include another sensor such as an electrocardiogram (ECG) sensor, an ultraviolet (UV) sensor, or a humidity sensor in addition to the temperature sensor. Thus, the patch-type sensor module according to one embodiment of the present invention may additionally acquire other pieces of biometric data together with information on the user's body temperature.

The communication unit may include a first communication module for authentication with the external communication module and a second communication module configured to transmit the information measured through the sensing unit such that, even when a physical switch is omitted, the communication unit may be driven.

An incised portion in which a plate-shaped battery is disposed may be formed in the flexible circuit board such that a thickness of the plate-shaped battery corresponding to a thickness of the flexible circuit board may be accommodated by the incised portion to reduce an overall thickness of the patch-type sensor module.

The power supply unit may be a rechargeable secondary battery, and the power supply unit may be recharged using a wireless power transmission method.

Meanwhile, the patch-type sensor module may further include a base substrate having flexibility and air permeability, and a medicinal solution layer disposed on one surface of the base substrate. Consequently, it is possible to acquire biometric data and, simultaneously, obtain an effect of improving skin care.

Advantageous Effects

In accordance with a patch-type sensor module according to the present invention, biometric data acquired through a sensor can be transmitted to the outside using a communication module such that a status of a user can be confirmed and monitored in real time. Consequently, the biometric data can be continuously acquired and it is possible to take prompt action in case of emergency.

Further, in accordance with the patch-type sensor module according to the present invention, in a case in which user authentication is performed through the communication module, a supply of power is initiated and thus a physical driving button can be omitted. Consequently, the patch-type sensor module can be implemented in a thin shape.

Moreover, in accordance with the patch-type sensor module according to the present invention, a battery can be charged through a wireless power transmission method such that the battery can be easily charged and can be continuously used without replacement.

DESCRIPTION OF DRAWINGS

FIG. 2 is a diagram illustrating a state in which a release film is separated in

FIG. 1.

MODES OF THE INVENTION

Hereinafter, embodiments of the present invention will be fully described in detail which is suitable for easy implementation by those skilled in the art to which the present invention pertains with reference to the accompanying drawings. The present invention may be implemented in various different forms, and thus it is not limited to the embodiments which will be described herein. In the drawings, some portions not related to the description will be omitted in order to clearly describe the present invention, and the same or similar reference numerals are assigned to the same or similar components throughout this disclosure.

As shown in FIGS. 1 to 16, a patch-type sensor module 100, 200, 300, or 400 according to one embodiment of the present invention includes a flexible circuit board 110, a power supply unit 120, a sensing unit 130 or 230, a communication unit 140, a control unit 150, and a protection member 160.

The flexible circuit board 110 is a substrate on which various circuit elements and circuit patterns are mounted and may be a known flexible printed circuit board (FPCB) having flexibility and using polyimide (PI), polyethylene terephthalate (PET), or the like. Here, the circuit element may be an element in the form of a chipset performing a predetermined function.

In this case, the flexible circuit board 110 may be in the form of a typically rectangular plate and may include an incised portion 112 having a predetermined area. For example, as shown in FIGS. 1, 7, 9, and 16, the incised portion 112 may be formed to be incised inward from one of four corners of the flexible circuit board 110.

The power supply unit 120 electrically connected to the flexible circuit board 110 may be disposed in the incised portion 112. Consequently, the incised portion 112 may accommodate all or a part of a thickness of the power supply unit 120. Thus, the thickness of the power supply unit 120 which is provided in the form of a known battery may be accommodated through the incised portion 112 such that thinness may be implemented.

The power supply unit 120 may be electrically connected to the flexible circuit board 110 to provide driving power required to drive the circuit elements mounted on the flexible circuit board 110.

The power supply unit 120 may be in the form of being stacked on one surface of the flexible circuit board 110. Alternatively, as described above, the power supply unit 120 may be electrically connected to the flexible circuit board 110 in a state of being disposed on the incised portion 112.

For example, the power supply unit 120 may be a known coin battery or a square-shaped battery. Alternatively, the power supply unit 120 may be a plate-shaped flexible battery so as to increase a capacity thereof while reducing an overall weight and a volume. As a specific example, the power supply unit 120 may be a known paper battery or a known pouch-type battery.

That is, in the patch-type sensor modules 100, 200, 300, and 400 according to one embodiment of the present invention, since the power supply unit 120 is implemented as a plate-shaped flexible battery, an overall weight may be reduced while securing a sufficient power capacity for driving. Further, since the power supply unit 120 is implemented as a thin flexible battery, even when the power supply unit 120 is stacked on one surface of the flexible circuit board 110, a total thickness of the patch-type sensor module may be reduced. In addition, as described above, in a case in which the thin flexible battery is disposed in the incised portion 112, all or a part of a thickness of the thin flexible battery may be accommodated through the incised portion 112 such that the thickness of the patch-type sensor module may be further reduced.

In this case, the power supply unit 120 may be a primary battery or a reusable secondary battery. Further, when the power supply unit 120 is configured with a secondary battery, the power supply unit 120 may be recharged using a wireless power transmission method.

Figure 7:
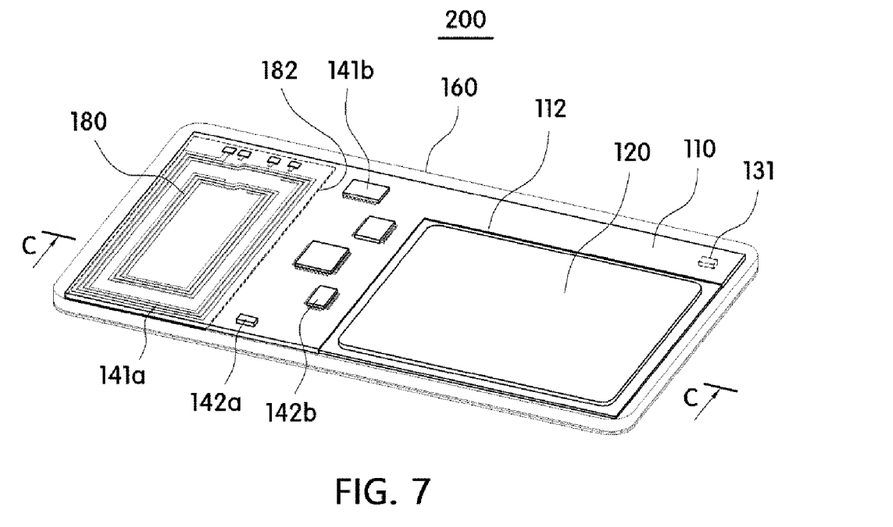
FIG. 7 is a schematic diagram illustrating a patch-type sensor module in which a wireless power reception antenna is included in FIG. 1.
Figure 15:
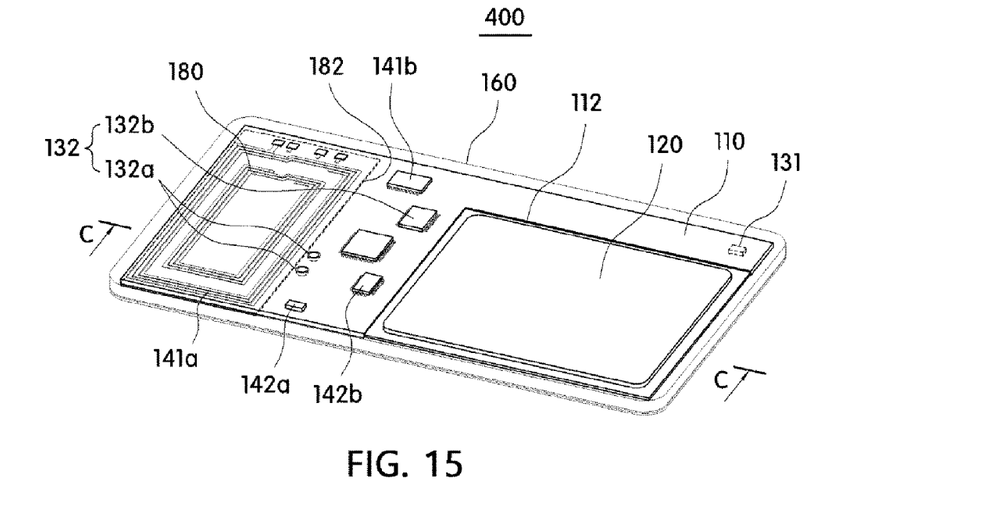
FIG. 15 is a schematic diagram illustrating a patch-type sensor module in which a wireless power reception antenna is included in FIG. 9.

For example, as shown in FIGS. 7 and 15, in the patch-type sensor module 200 or 400 according to one embodiment of the present invention, a wireless power reception antenna 180 may be formed in a predetermined pattern on one surface of the flexible circuit board 110. Thus, the wireless power reception antenna 180 may receive wireless power transmitted from an external charging device and then supply the received power to the power supply unit 120 such that the power supply unit 120 may be recharged. Here, any one of a known magnetic induction method, a known magnetic resonance method, and a known ultrasonic method may be applied as a wireless charging method.

The wireless power reception antenna 180 may be directly formed in a predetermined pattern on one surface of the flexible circuit board 110 by printing a conductive material thereon.

In this case, the flexible circuit board 110 may include a wireless charging circuit (not shown) for recharging the power supply unit 120 using the power received through the wireless power reception antenna 180. In addition, the flexible circuit board 110 may further include a protection circuit to prevent overcharge during charging of the power supply unit 120. The wireless charging circuit and the protection circuit may be controlled by the driving of the control unit 150.

Thus, in the patch-type sensor modules 200 and 400 according to one embodiment of the present invention, the power supply unit 120 may be recharged through the wireless charging method. Consequently, even when the power supply unit 120 is completely discharged, it is possible to reuse the power supply unit 120 without replacement thereof and to secure stable driving power.

Figure 8:
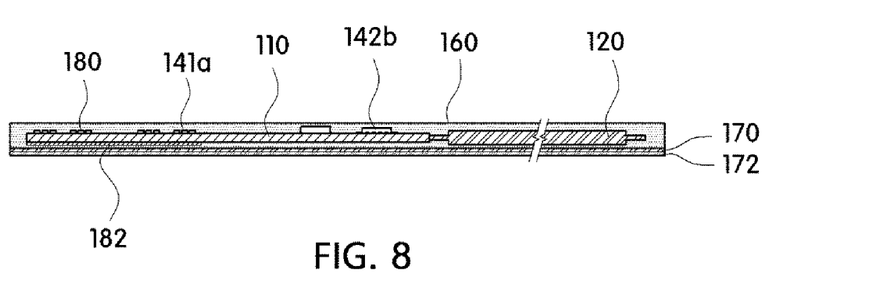
FIG. 8 is a cross-sectional view taken along line C-C of FIG. 7.
Figure 16:
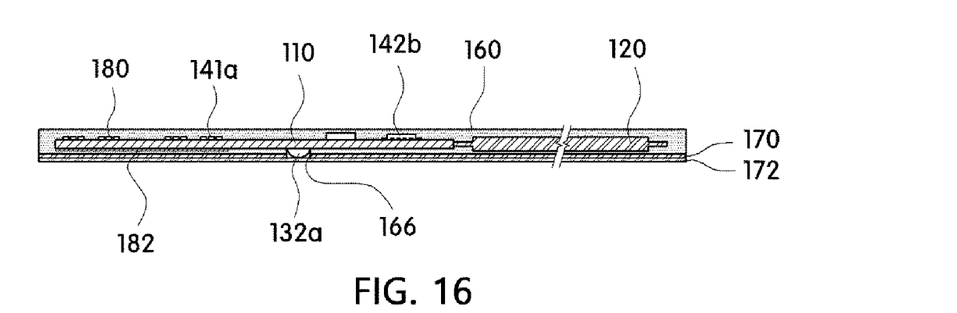
FIG. 16 is a cross-sectional view taken along line B-B of FIG. 15.

Meanwhile, in a case in which each of the patch-type sensor modules 200 and 400 according to one embodiment of the present invention includes the wireless power reception antenna 180 for wireless charging, as shown in FIGS. 8 and 16, in the patch-type sensor modules 200 and 400, a known shielding sheet 182 may be disposed in a region corresponding to the wireless power reception antenna 180 so as to shield a magnetic field and to increase charging efficiency. Here, the shielding sheet may be a plate-shaped sheet, and all of known magnetic materials used as a shielding sheet, such as ferrite, an amorphous material, a polymer, and the like may be used as the shielding sheet. Further, the shielding sheet may be in the form of being flaked and separated into a plurality of micro-pieces so as to secure flexibility.

The sensing unit 130 or 230 may be mounted on one surface of the flexible circuit board 110 to acquire various pieces of information, including a user's body temperature, from a user's body.

The sensing unit 130 or 230 may be electrically connected to the control unit 150 and may be driven under the control of the control unit 150. The information obtained through the sensing unit 130 or 230 may be transmitted to an external device through the communication unit 140 which will be described below.

Figure 6:
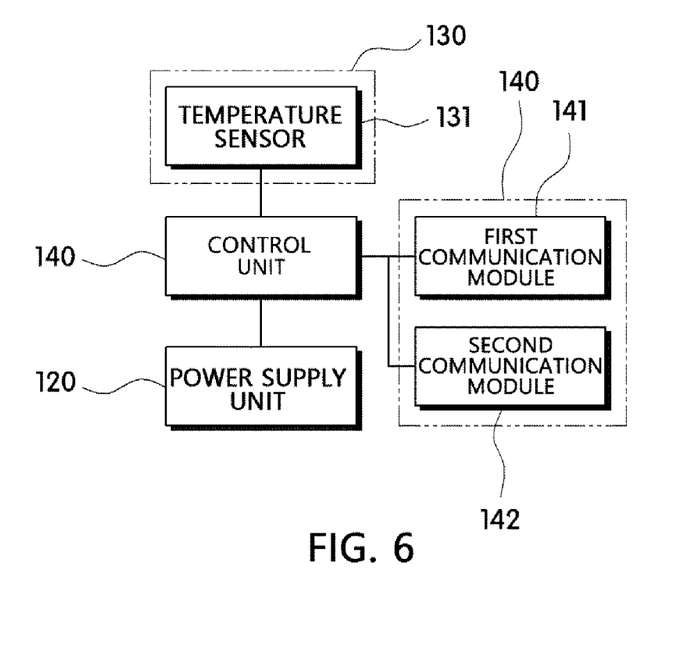
FIG. 6 is a block diagram showing an electrical connection relationship between a control unit and other components in FIG. 1.
Figure 14:
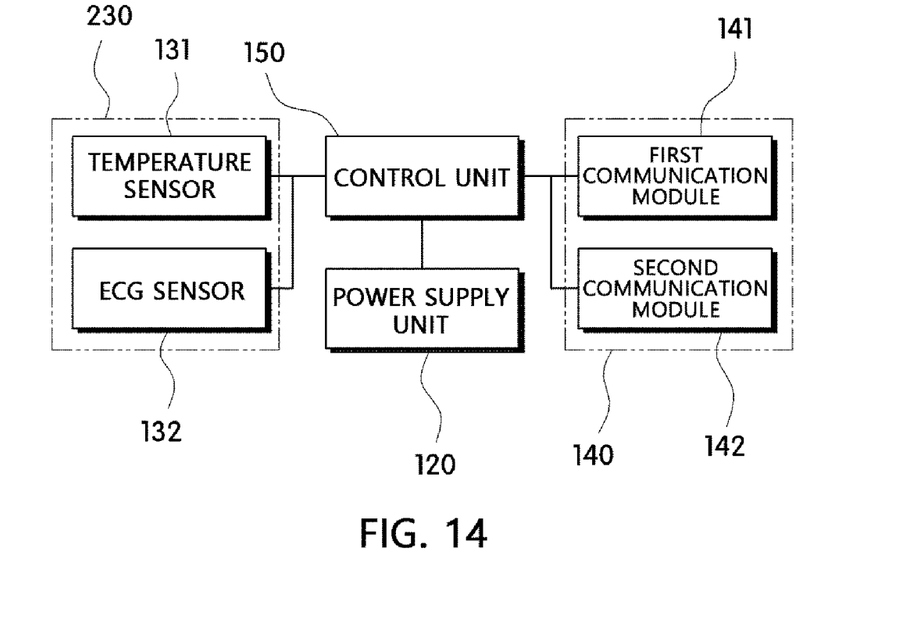
FIG. 14 is a block diagram showing an electrical connection relationship between a control unit and other components in FIG. 9.

In this case, as shown in FIG. 6, the sensing unit 130 or 230 may be configured with only a temperature sensor 131. Alternatively, as shown in FIG. 14, the sensing unit 130 or 230 may be configured with a plurality of sensors 131 and 132 so as to acquire various pieces of information.

That is, in addition to the temperature sensor 131 configured to measure a user's body temperature, the sensing unit 230 may include at least another sensor 132 configured to sense other pieces of information excluding the user's body temperature.

For example, the another sensor 132 may include one or more among an electrocardiogram (ECG) sensor, an ultraviolet (UV) sensor, and a humidity sensor to acquire information on a user's electrocardiogram or heartbeat, an amount of UV rays applied to a user's skin, a moisture content of the user's skin, and the like. Accordingly, the patch-type sensor modules 300 and 400 according to one embodiment of the present invention may include the plurality of sensors 131 and 132 configured to sense different information, and thus various pieces of biometric data may be sensed through a single device.

In this case, the sensing unit 130 or 230 may be exposed to a user's body so as to smoothly sense the biometric data.

Figure 5:
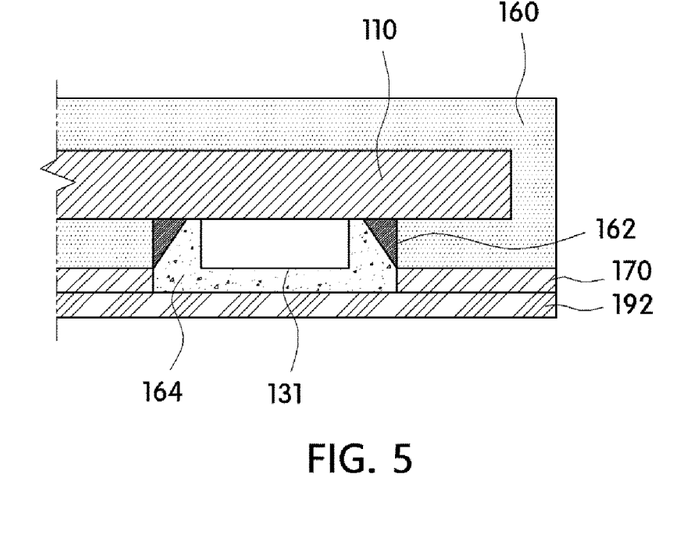
FIG. 5 is a cross-sectional view taken along line B-B of FIG. 3.
Figure 13:
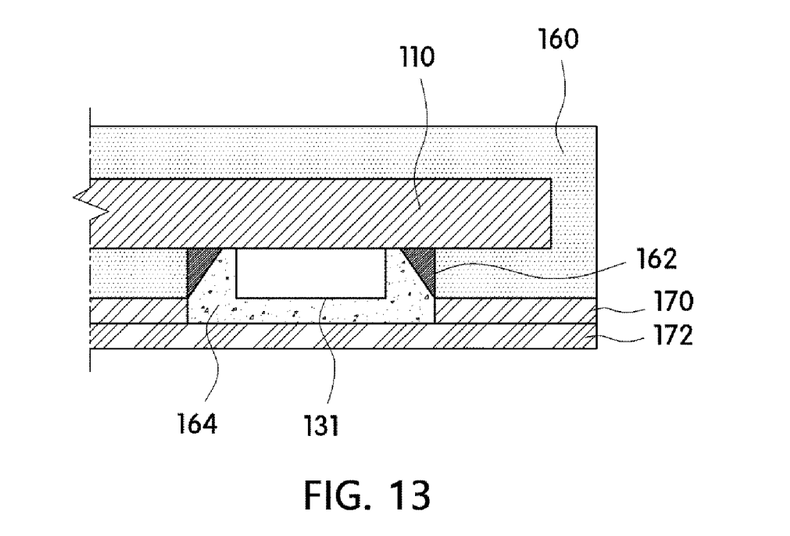
FIG. 13 is a cross-sectional view taken along line E-E of FIG. 11.

As a specific example, as shown in FIGS. 5 and 13, the temperature sensor 131 may be mounted on a bottom surface of both surfaces of the flexible circuit board 110. When the patch-type sensor module 100, 200, 300, or 400 according to one embodiment of the present invention is attached to the user's body, the temperature sensor 131 may be exposed to the user's body.

Figure 9:
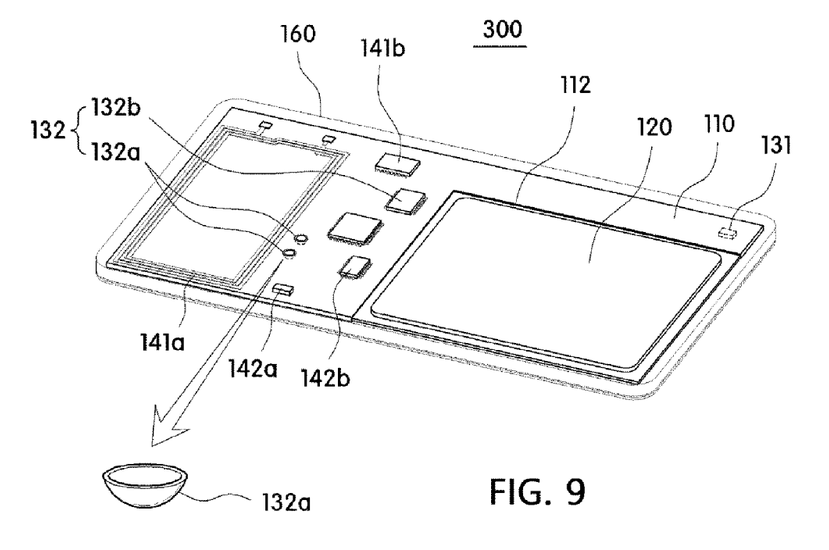
FIG. 9 is a schematic diagram illustrating a case in which a sensing unit includes a plurality of sensors in a patch-type sensor module according to one embodiment of the present invention.

In addition, in a case in which the another sensor is an ECG sensor 132 configured to measure an electrocardiogram or heartbeat of the user, as shown in FIGS. 9 and 15, the ECG sensor 132 may include a driving chip 132b, which is mounted on one surface of the flexible circuit board 110, and a pair of electrodes 132a, which are mounted on the other surface of the flexible circuit board 110 so as to be electrically connected to the driving chip 132b. In this case, at least a part of the pair of electrodes 132a may be exposed to the outside from one surface of the protection member 160 so as to come into direct contact with the user's body.

Figure 1:
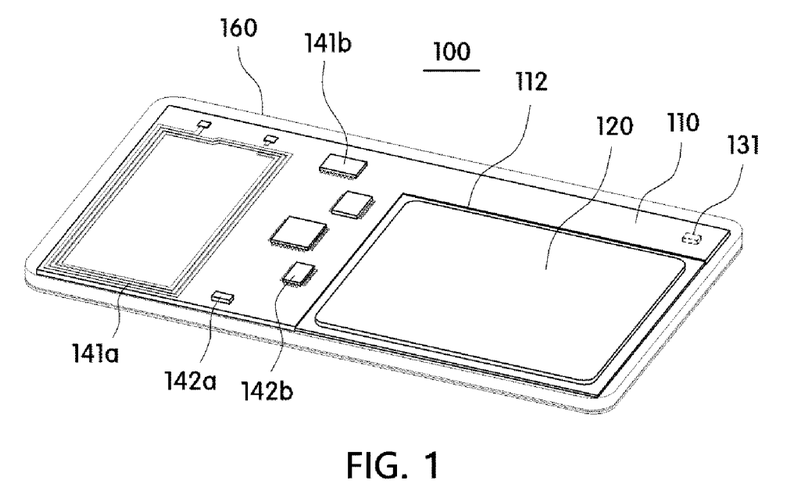
FIG. 1 is a schematic diagram illustrating a patch-type sensor module according to one embodiment of the present invention.
Figure 2:
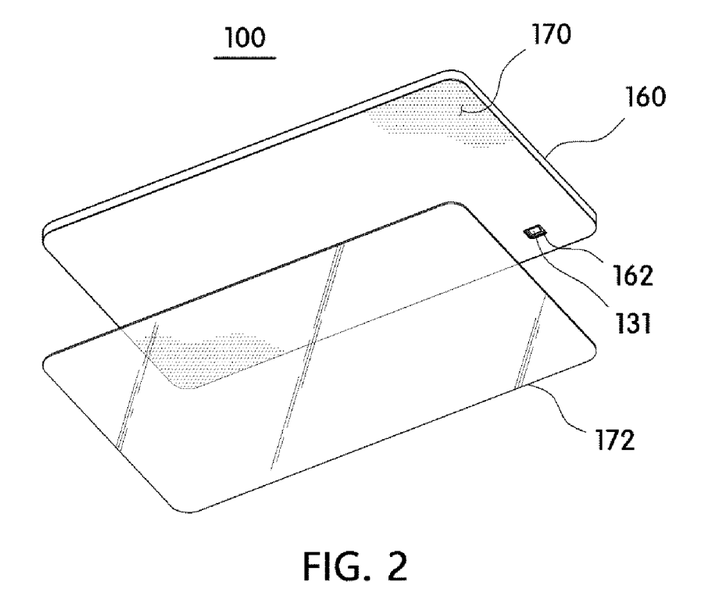
Figure 3:
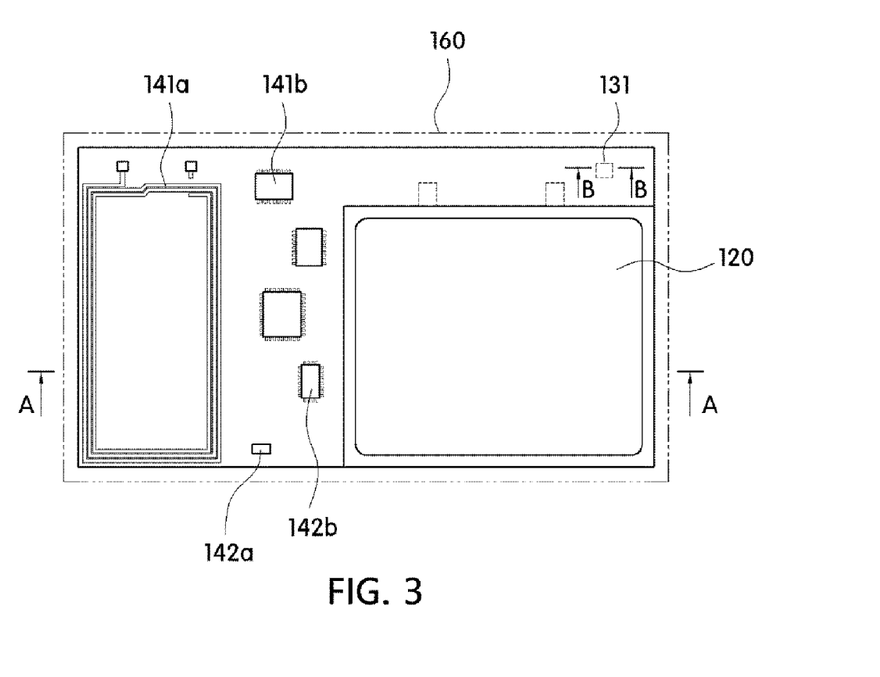
FIG. 3 is a plan view of FIG. 1.
Figure 4:
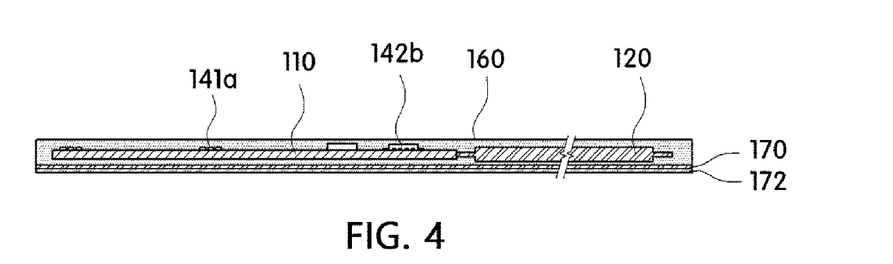
FIG. 4 is a cross-sectional view taken along line A-A of FIG. 3.
Figure 10:
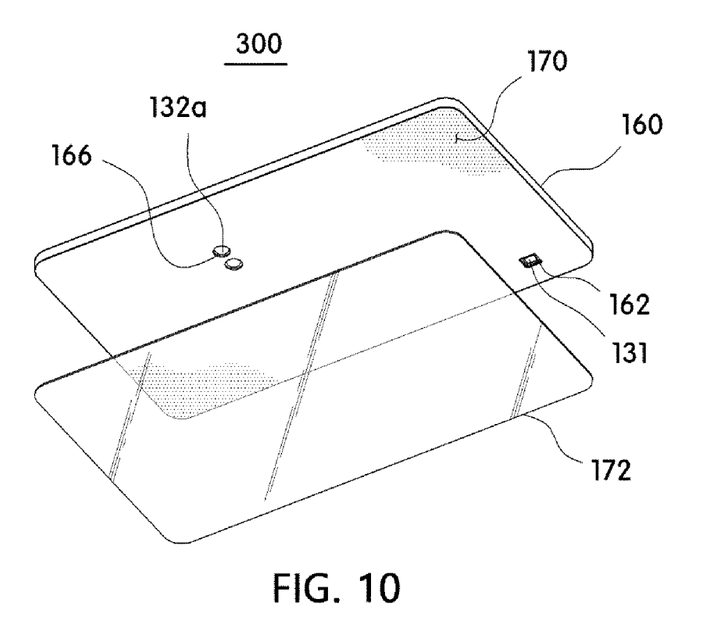
FIG. 10 is a diagram illustrating a state in which a release film is separated in FIG. 9.
Figure 11:
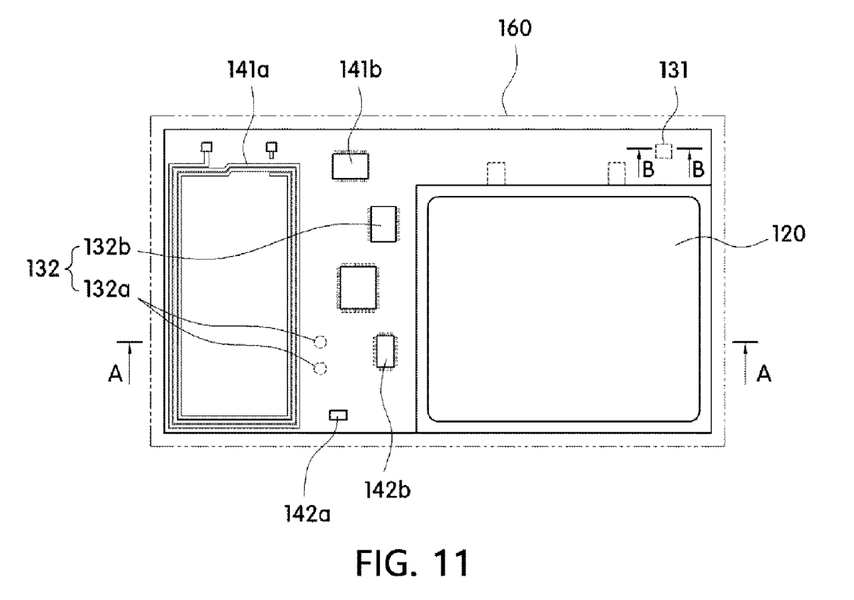
FIG. 11 is a plan view of FIG. 9.

To this end, as shown in FIGS. 2 and 10, an exposure hole 162 may be formed to pass through the protection member 160 in a region corresponding to the temperature sensor 131. In addition, when each of the patch-type sensor modules 300 and 400 includes another sensor 132 in addition to the temperature sensor 131, as shown in FIG. 10, arrangement holes 166 having a predetermined area may be formed to pass through the protection member 160 in regions corresponding to the pair of electrodes 132a.

Thus, when each of the patch-type sensor modules 100, 200, 300, and 400 according to one embodiment of the present invention is attached to the user's skin via an adhesive member 170 disposed on one surface of the protection member 160, the temperature sensor 131 and the pair of electrodes 132a may face the user's skin or come into direct contact therewith through the exposure hole 162 and the arrangement holes 166 such that desired information may be smoothly sensed.

In this case, as shown in FIGS. 5 and 13, a sealing member 164 may fill the exposure hole 162 so as to block moisture from flowing from the outside to the flexible circuit board 110. The sealing member 164 may fill the exposure hole 162 to seal a gap between the exposure hole 162 and the temperature sensor 131 along an edge of the exposure hole 162 or to fill the exposure hole 162 to completely cover the temperature sensor 131.

Figure 12:
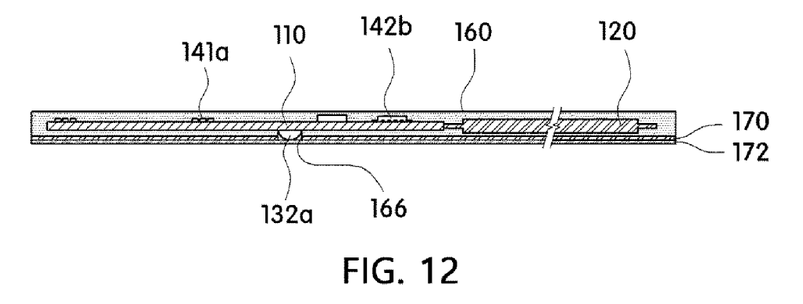
FIG. 12 is a cross-sectional view taken along line D-D of FIG. 11.

Further, as shown in FIG. 9, the pair of electrodes 132a may be formed to be inclined from an edge to a central portion and thus the pair of electrodes may have a dome shape in which the central portion protrudes convexly in one direction. Preferably, the central portion may be in the form of being convex to the user's skin. In addition, as shown in FIGS. 12 and 16, at least a part of the pair of electrodes 132a may be formed to have a height protruding outward from the arrangement hole 166 such that the pair of electrodes 132a may be mounted on one surface of the flexible circuit board 110. Thus, the pair of electrodes 132a may be brought into smooth contact with the user's skin.

Accordingly, when the patch-type sensor module 100, 200, 300, or 400 according to one embodiment of the present invention is attached to the user's skin, even when the attached portion is bent, the central portions of the pair of electrodes 132a may always maintain a state of being brought into contact with the user's skin such that a required biological signal may be smoothly sensed from the user's body.

Meanwhile, when the sensing unit 230 is composed of a plurality of sensors, although the ECG sensor has been described in detail as one aspect of another sensor, the position and the shape of the other sensor are not limited to the above description. When the another sensor is a UV sensor or a humidity sensor, an installation position of the other sensor may be appropriately changed according to information which will be sensed. For example, the UV sensor and the humidity sensor may be mounted by employing a method which is the same as a method of mounting the above-described temperature sensor 131. A surface on which the UV sensor and the humidity sensor are mounted on the flexible circuit board 110 may be the same surface or an opposite surface on which the temperature sensor 131 is mounted.

The communication unit 140 may be mounted on one surface of the flexible circuit board 110 and may be electrically connected to the control unit 150. The communication unit 140 may serve as a switch which allows power to be supplied using a wake-up function in addition to a function of providing data, which is measured by the sensing unit 130 or 230, to an external electronic device.

That is, when the user is authenticated through the communication unit 140, the patch-type sensor modules 100, 200, 300, and 400 according to one embodiment of the present invention may supply power from the power supply unit 120 to the control unit 150.

Thus, an ON/OFF operation of the power configured to drive the patch-type sensor modules 100, 200, 300, and 400 according to one embodiment of the present is not required so that a physical ON/OFF button may be omitted. Consequently, it is possible to simplify a configuration of a product and implement thinness of the product by omitting the physical ON/OFF button.

To this end, the communication unit 140 may include a first communication module 141 to perform user authentication through wireless communication with an external electronic device, and a second communication module 142 to transmit information measured by the sensing unit 130 or 230 through a pairing with an external communication module included in the external electronic device.

In the present invention, the external electronic device may be a portable electronic device, such as a smart phone, a tablet personal computer (PC) or the like, a server, or a medical device. Further, the external electronic device may be in a form in which a communication module corresponding to at least one of the first communication module 141 and the second communication module 142 is embedded.

For example, the first communication module 141 may be a near field communication (NFC) antenna module, the second communication module 142 may be a Bluetooth antenna module, and the external electronic device may be a smart phone in which the NFC antenna module and the Bluetooth antenna module are embedded.

To this end, an NFC antenna 141*a* may be formed in a pattern on one surface of the flexible circuit board 110, and a Bluetooth antenna 142*a* may be mounted outside the NFC antenna 141*a*. Further, driving chips 141*b* and 142*b* configured to respectively drive the NFC antenna 141*a* and the Bluetooth antenna 142*a* may be mounted on one surface of the flexible circuit board 110.

That is, when the external electronic device is in proximity, the patch-type sensor modules 100, 200, 300, and 400 according to one embodiment of the present invention may perform authentication of the user through the NFC antenna 141*a*. Further, when the user is authenticated through the NFC antenna 141*a*, power may be supplied from the power supply unit 120 to the control unit 150 and the Bluetooth antenna module may be operated such that pairing may be performed on the Bluetooth antenna module with the Bluetooth antenna module included in the smartphone.

Thus, data measured by the sensing unit 130 or 230 may be transmitted to the smartphone paired through the second communication module 142. Consequently, the user may confirm the measured data by the sensing unit 130 or 230 in real time through the smartphone. Further, the data transmitted to the smartphone may be stored in the smartphone or may be separately stored in a separate server or other electronic device using a network to which the smartphone is connected.

However, the first communication module 141 which may be applied to the present invention for user authentication is not limited to the NFC antenna module, and various known wireless communication methods such as a radio frequency identification (RFID) communication method, an infrared data association (IrDA) communication method, an ultra wideband (UWB) communication method, a long range (LoRa) communication method, a RADAR communication method, a low power wireless communication method, a WiFi communication method, and the like may be applied to the present invention for user authentication. According to a communication method applied to the present invention for user authentication, a suitable chipset may be mounted on the flexible circuit board 110. Further, the first communication module 141 may be a long distance communication module performing wireless communication according to a communication method including system management (SM), general packet radio service (GPRS), enhanced data GSM environment (EDGE), long term evolution-advanced (LTE-A), LTE, code division multiple access (CDMA), wideband CDMA (WCDMA), evolution-data optimized (EVDO), wireless broadband Internet (Wibro), Mobile WiMax, or the like.

The control unit 150 may generate valid information based on the signal sensed by the sensing unit 130 or 230 and transmit the generated valid information to the outside and control an overall operation of the patch-type sensor module 100, 200, 300, or 400.

To this end, the control unit 150 may include at least one circuit element mounted on one surface of the flexible circuit board 110.

For example, the circuit element may be a chipset such as a main control unit (MCU) which is capable of generating data based on the signal measured through the sensing unit 130 or 230 and transmitting the data to the outside.

As described above, in the patch-type sensor modules 100, 200, 300, and 400 according to one embodiment of the present invention, various pieces of data including information on the user's body temperature measured through the sensing unit 130 or 230 may be transmitted to a server or an electronic device present at a long distance or a short distance through the second communication module 142.

Thus, the server or the electronic device may collect and monitor biometric data of the user in real time by storing the data transmitted from the second communication module 142 and updating various pieces of information including the information on the user's body temperature in real time or periodically.

Consequently, the biometric data of the user may be analyzed and utilized through the data accumulated in the server or the electronic device such that healthcare of the user may be performed.

In addition, when the user is a target requiring a real-time or periodic check of biometric data, such as a patient or an elderly person, it is possible to perform real-time or periodic monitoring through the biometric data of the user transmitted to the server or the electronic device, and when there is an emergency, it is possible to take prompt action for relief.

That is, the patch-type sensor modules 100, 200, 300, and 400 according to one embodiment of the present invention may be applied to healthcare systems, silver industries, and medical industries.

Meanwhile, the patch-type sensor modules 100, 200, 300, and 400 according to one embodiment of the present invention may include the protection member 160 to prevent the circuit patterns, the circuit elements, or the power supply unit 120, which are mounted on the flexible circuit board 110, from being exposed to the outside.

The protection member 160 may be made of a material having flexibility such that, even when attached to a bent portion, the patch-type sensor module 100, 200, 300, or 400 according to one embodiment of the present invention may secure flexibility so as to maintain a tightly adhered state.

For example, the protection member 160 may be formed of a fluoropolymer resin such as PET, polypropylene (PP), polyethylene (PE), or the like or may be formed as a sheet such as release paper or formed as a molding covered with a resin material made of silicone or polyurethane. However, it is noted that the material of the protection member 160 is not limited thereto, and any material having flexibility may be used without limitation.

Further, the protection member 160 may be formed of a material having air permeability in addition to flexibility.

As a specific example, the protection member 160 may be a nanofiber web in which nanofibers including synthetic polymers are accumulated. That is, in order to allow air to freely pass through while blocking moisture, the protection member 160 may be formed of a nanofiber web having micropores, and the nanofiber web may be formed in a three-dimensional network structure.

Meanwhile, the adhesive member 170 is provided on one surface of the protection member 160 so that the patch-type sensor module 100, 200, 300, or 400 according to one embodiment of the present invention may be directly attached to the user's body.

Here, the adhesive member 170 may be an non-base material type member such as a gluing agent or an adhesive. Alternatively, the adhesive member 170 may be a base material type member in which both surfaces of a base material such as a double-sided tape are coated with the gluing agent or the adhesive.

Preferably, the adhesive member 170 may be formed to be detachable so as to enable the reuse of the patch-type sensor modules 100, 200, 300, or 400 according to one embodiment of the present invention.

In this case, a separate release film 172 may be disposed on one surface of the adhesive member 170 to prevent the adhesive member 170 from being exposed to the outside when not in use. When the patch-type sensor module 100, 200, 300, or 400 according to one embodiment of the present invention is attached to the user's body, the release film 172 may be removed.

Meanwhile, patch-type sensor modules 500 and 600 according to exemplary embodiments of the present invention may be formed to include a base substrate 191 and a medicinal solution layer 192.

Figure 17:
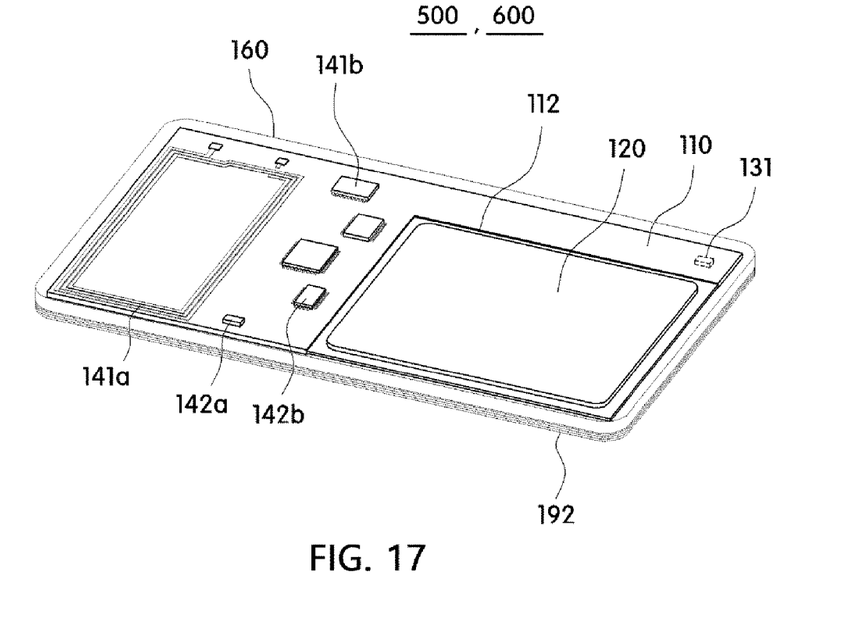
FIG. 17 is a schematic diagram illustrating a case in which a patch-type sensor module includes a base substrate and a medicinal solution layer according to one embodiment of the present invention.
Figure 18:
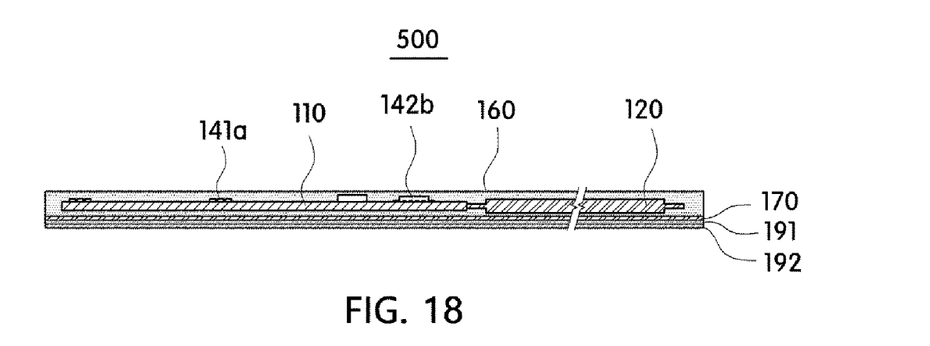
FIG. 18 is a cross-sectional view taken along line G-G of FIG. 17 that illustrates a stacked relationship of a protection member, a base substrate, and a medicinal solution layer.
Figure 19:
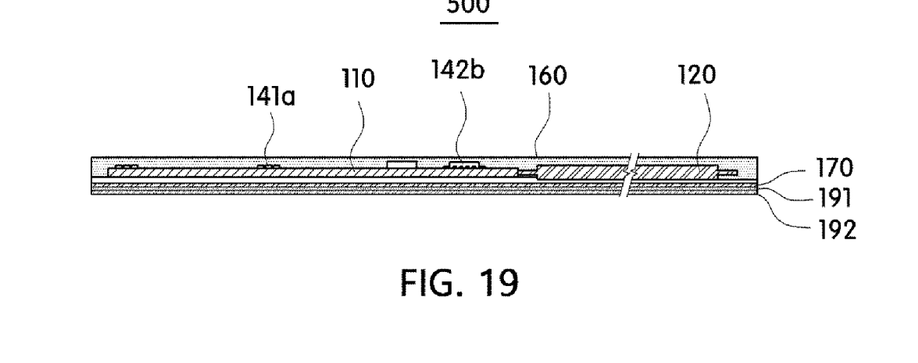
FIG. 19 is a cross-sectional view taken along line G-G of FIG. 17 that illustrates another stacked relationship of the protection member, the base substrate, and the medicinal solution layer.

That is, as shown in FIGS. 17 to 19, the patch-type sensor modules 500 and 600 according to the present embodiment may include a flexible circuit board 110, a power supply unit 120, a sensing unit 330, a communication unit 140, a control unit 150, a protection member 160, and the base substrate 191 and the medicinal solution layer 192 may be sequentially disposed on one side of the protection member 160.

Accordingly, unlike the above-described embodiments, in the present embodiment, the medicinal solution layer 192 may be brought into direct contact with the user's skin.

In the present embodiment, the flexible circuit board 110, the power supply unit 120, the sensing unit 330, the communication unit 140, the control unit 150, and the protection member 160 are the same as those applied to the above-described embodiments, and thus detailed descriptions thereof will be omitted. Further, the sensing unit 330 in the present embodiment may be the sensing unit 130 shown in FIGS. 1 to 8 or the sensing unit 230 shown in FIGS. 9 to 16.

The base substrate 191 may support the medicinal solution layer 192 disposed on one surface of the base substrate 191. To this end, the base substrate 191 may be formed as a plate including a first surface and a second surface, each of which has a predetermined area. One surface of the base substrate 191 may be attached to one surface of the protection member 160 via the adhesive member 170 or be attached to one surface of the flexible circuit board 110.

For example, as shown in FIG. 18, the base substrate 191 may be attached to a bottom surface of the protection member 160 via the adhesive member 170.

Alternatively, as shown in FIG. 19, the base substrate 191 may be attached to one surface of the flexible circuit board 110 via the adhesive member 170. In this case, the protection member 160 may be formed to prevent remaining portions except for the bottom surface of the flexible circuit board 110 and the power supply unit 120 from being exposed to the outside.

In this case, the base substrate 191 applied to the present invention may have flexibility, moisture blockability, and air permeability. To this end, the base substrate 191 may be formed of a nanofiber web having micropores P.

Figure 20:
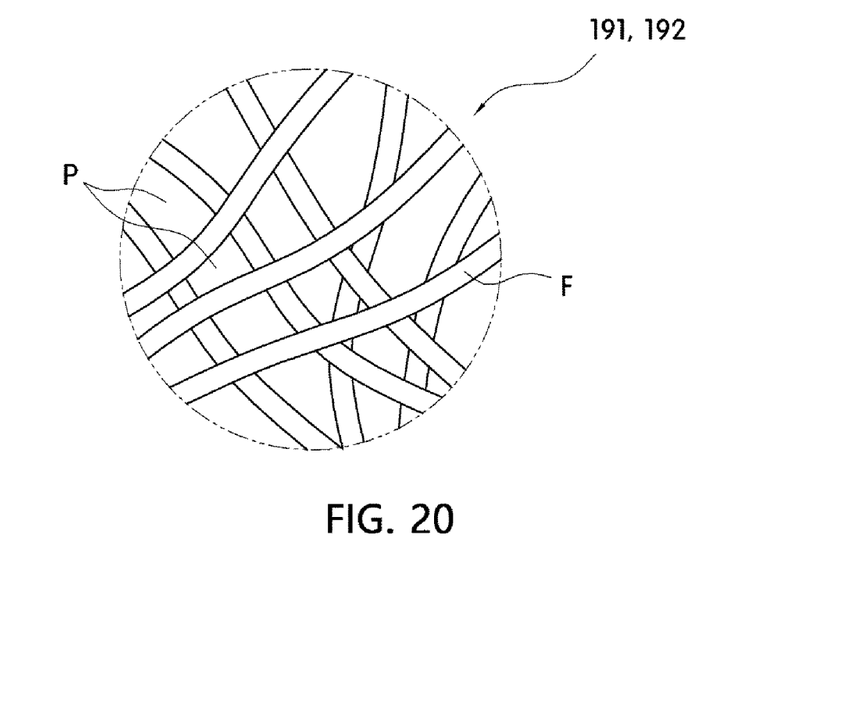
FIG. 20 is a schematic diagram illustrating a base substrate and a medicinal solution layer which may be applied to FIG. 17.

For example, as shown in FIG. 20, the base substrate 191 may be a nanofiber web in which nanofibers F including synthetic polymers are accumulated. That is, in order to allow air to freely pass through while blocking movement of moisture, the base substrate 191 may be formed of a nanofiber web having the micropores P, and the nanofiber web may be formed in a three-dimensional network structure. In this case, an average pore diameter of the micropores P may be 10 μm or less.

Specifically, the base substrate 191 may be a single-layer nanofiber web accumulated so as to have the micropores P by electrically spinning a spinning solution in which a synthetic polymer and a solvent are mixed. Here, the solvent may be water or alcohol. Alternatively, in addition to the water or alcohol, the solvent may be an organic solvent.

In this case, the synthetic polymer may be a fiber-formable polymer capable of being electrically spun while not being dissolved by the solvent so as to implement a nanofiber web through electric spinning. Thus, even when the base substrate 191 is in contact with the solvent, the base substrate 191 may be not dissolved by the solvent and maintain a form of the nanofiber web. Consequently, the base substrate 191 may be attached to the skin for a long period of time. Further, even when a long period of time elapses after the base substrate 191 is attached to the user's skin, air may smoothly flow to the user's skin through the micropores P such that skin problems such as festering occurring due to air blocking may be prevented.

In addition, in a case in which the medicinal solution layer 192 which is water-soluble is disposed on one surface of the base substrate 191 and is released in a liquid phase or a gel phase by being in contact with a solvent applied on the skin of the user, the base substrate 191 may be not dissolved by the solvent and maintain the form of the nanofiber web. Consequently, the base substrate 191 may serve to support the released medicinal solution layer 192. Therefore, when the protection member 160 is made of a material having air permeability, the patch-type sensor module 500 or 600 according to one embodiment of the present invention may prevent effective components contained in the medicinal solution layer 192 from passing through the base substrate 191 to leak to the outside while supplying air from the outside to a body part of the user through the micropores formed in the base substrate 191, thereby promoting penetration of the effective components into the user's skin.

Further, the base substrate 191 may be formed such that the average pore diameter of the micropores has 10 μm or less. Consequently, the base substrate 191 may diffuse reflection of light passing through the micropores. Accordingly, even when a functional material such as an ultraviolet blocking component is not added, the base substrate 191 may have an effect of blocking ultraviolet rays through the micropores.

In the present invention, the synthetic polymer is not particularly limited as long as it is a resin which can be dissolved in a solvent for electric spinning, can form nanofibers by electric spinning, and is not dissolved by a solution. As a non-limiting example, the synthetic polymer may include one or more selected from among polyvinylidene fluoride (PVDF), poly (vinylidene fluoride-co-hexafluoropropylene), a perfluoropolymer, polyvinyl chloride, polyvinylidene chloride, a copolymer thereof, polyethylene glycol derivatives including polyethylene glycol dialkyl ether and polyethylene glycol dialkyl ester, polyoxide including poly(oxymethylene-oligo-oxyethylene), polyethylene oxide, and polypropylene oxide, copolymers including polyvinyl acetate, poly(vinylpyrrolidone-vinyl acetate), polystyrene, and polystyrene acrylonitrile, polyacrylonitrile copolymers including polyacrylonitrile (PAN) and polyacrylonitrile methyl methacrylate, and a polymethyl methacrylate copolymer, or a mixture of two or more selected from thereamong.

The medicinal solution layer 192 is formed on one surface of the base substrate 191. The medicinal solution layer 192 may be in direct contact with the skin of the user to provide an advantageous effective component thereto.

To this end, the medicinal solution layer 192 may be a nanofiber web accumulated to allow the nanofibers F including water-soluble polymers to have the micropores P by electrically spinning a spinning solution in which a water-soluble polymer, a functional material, and a solvent are mixed at an appropriate ratio (see FIG. 20).

That is, the medicinal solution layer 192 may be implemented in the form of a nanofiber web through a spinning solution in which a water-soluble polymer material and a functional material are mixed. Accordingly, when the medicinal solution layer 192 is attached to the skin on which a solvent is applied and then is in contact with the solvent, the medicinal solution layer 192 may be changed into a released state. Consequently, the functional material contained in the medicinal solution layer 192 may be absorbed into the skin, and the water-soluble polymer material may be absorbed into the base substrate 191.

Here, the water-soluble polymer material is not particularly limited as long as it is a polymer material which is dissolved in water or alcohol and can form nanofibers through electric spinning. As a non-limiting example, the water soluble polymer material may be a mixture including one or more selected from among polyvinyl alcohol (PVA), polyvinyl pyrrolidone (PVP), polyethylene oxide (PEO), carboxyl methyl cellulose (CMC), starch, polyacrylic acid (PAA), and hyaluronic acid.

Further, the functional material may be a dry storage material which is difficult to store in a liquid phase. In addition, when the water-soluble polymer is dissolved, the dry storage material may be released in a state of a liquid phase or a phase such that the dry storage material may be smoothly absorbed into the skin of the user. For example, the dry storage material may be a vitamin, an enzyme, a protein, a peptide-vitamin C derivative, or the like. Usually, the above-described dry storage material has a property of being decomposed only in a liquid phase. However, it is difficult to store the dry storage material in a liquid state for a long period of time.

In the present invention, the dry storage material which is difficult to store in a liquid phase is included in the spinning solution together with the water-soluble polymer material and the solvent, the spinning solution containing the dry storage material is formed into nanofibers through electric spinning, and the medicinal solution layer 192 may be configured in the form of a nanofiber web such that the dry storage material may be bound in a dry state in the nanofibers constituting the medicinal solution layer 192.

Thus, the dry storage material which is difficult to store in a liquid phase may be stored for a long period of time, and, when the water-soluble polymer is dissolved by the solvent, the functional material in a dry state may be released together with the water-soluble polymer. Consequently, the functional material may be transferred to the skin and smoothly penetrate into the skin.

That is, when the patch-type sensor module 500 or 600 according to one embodiment of present invention is attached to the user's skin, the water-soluble polymer constituting the medicinal solution layer 192 may be dissolved by the solvent applied on the skin, and the functional material bound by the water-soluble polymer may be released. Accordingly, the released functional material may be absorbed into the skin, and the water-soluble polymer dissolved by the solvent may be absorbed into the base substrate 191.

In the present invention, the functional material is a material for skin care and wound care and may be a mixture including any one among ingredients that aid in skin whitening (arbutin, niacinamide, and ascoglucoside), ingredients that help to improve skin wrinkles (retinol and adenosine), an ingredient that helps to block ultraviolet rays (titanium dioxide), ingredients that aid in moisturizing and skin elasticity (a snail mucilage filtrate, acetyl hexapeptide, red ginseng collagen, aqua ceramide, regenerating peptide, and a galactomyces fermentation liquid), growth factors such as an epithelial growth factor (EGF) and a fibroblast growth factor (FGF), a protein for healing, and antimicrobial substances such as silver nano materials and chitosan. Alternatively, the functional material may be a mixture including one or more selected from among water-soluble collagen, vegetable platinum, tocopherol, xylitol, and a vegetable extract.

In this case, a predetermined ratio of oil may be contained in the spinning solution for forming the medicinal solution layer 192 so as to adequately control a time for which the medicinal solution layer 192 is dissolved when in contact with the solvent. Consequently, the patch-type sensor module 500 or 600 according to one embodiment of the present invention may control a drying time of the base substrate 191 attached to the user's skin.

Accordingly, the patch-type sensor modules 500 and 600 according to one embodiment of the present invention may each supply the advantageous effective ingredient to the user's skin through the medicinal solution layer 192 while collecting biometric data on the user's body temperature through the temperature sensor 330 such that it is possible to simultaneously achieve information acquisition and an effect of skin improvement.

The patch-type sensor modules 100, 200, 300, 400, 500, and 600 according to one embodiment of the present invention may each be implemented as a healthcare product or a medical product. Further, it is noted that the patch-type sensor modules 100, 200, 300, 400, 500, and 600 according to one embodiment of the present invention may be applied to not only clothing products such as vests, shoes, clothes, and the like but also wearable devices such as a smart watch and a smart glasses and may further be applied to a mask pack and the like.

In addition, although the ECG sensor, the UV sensor, and the humidity sensor have been described as other types of sensors which are capable of being applied to the present invention, the other types of sensors are not limited thereto and any known sensor may be applied as long as it can measure information relating to the user's body. Moreover, it is note that various known sensors capable of measuring an environment around the user in addition to the biometric data of the user may be applied.

The invention claimed is:

1. A patch-type sensor module comprising:
a power supply unit electrically connected to a flexible circuit board;
a sensing unit mounted on the flexible circuit board and including a temperature sensor configured to measure a user's body temperature;
a communication unit for allowing power to be supplied using a wake-up function and for transmitting information measured by the sensing unit to an external communication module through a pairing with the external communication module when power is supplied;
a control unit configured to control driving of the power supply unit, the sensing unit, and the communication unit; and
a protection member configured to prevent the flexible circuit board, the power supply unit, the sensing unit, the communication unit, and the control unit from being exposed to an outside,
wherein the flexible circuit board includes an incised portion having a predetermined area and formed to be incised inward in a thickness of the flexible circuit board; and
the power supply unit is disposed in the incised portion such that all of a thickness of the power supply unit corresponding to a thickness of the flexible circuit board is accommodated by the incised portion,
wherein the power supply unit is disposed in the incised portion and is not stacked on a surface of the flexible circuit board,
wherein the flexible circuit board comprises a pair of electrodes mounted on one surface thereof and configured to be convex to a user's skin, and
wherein the power supply contact pads are electrically connected to the flexible circuit board in the incised portion.

2. The patch-type sensor module of claim 1, wherein the sensing unit further includes at least another sensor configured to sense information different from that measured by the temperature sensor.

3. The patch-type sensor module of claim 2, wherein the at least another sensor includes at least one among an electrocardiogram (ECG) sensor, an ultraviolet (UV) sensor, and a humidity sensor.

4. The patch-type sensor module of claim 2, wherein: the pair of electrodes is disposed in arrangement holes formed to pass through the protection member.

5. The patch-type sensor module of claim 1, wherein the communication unit includes a first communication module for authentication with the external communication module and a second communication module configured to transmit information measured through the sensing unit.

6. The patch-type sensor module of claim 5, wherein:
the first communication module is a near field communication (NFC) antenna module; and
the second communication module is a Bluetooth antenna module.

7. The patch-type sensor module of claim 1, wherein:
the protection member includes an exposure hole formed to pass through a region corresponding to the temperature sensor; and
the temperature sensor is disposed in the exposure hole.

8. The patch-type sensor module of claim 7, wherein the exposure hole is filled with a sealing member configured to block an inflow of moisture from the outside to the flexible circuit board.

9. The patch-type sensor module of claim 1, wherein the power supply unit is a plate-shaped flexible battery.

10. The patch-type sensor module of claim 1, wherein a wireless power reception antenna configured to receive external wireless power and recharge the power supply unit is formed in a pattern on one surface of the flexible circuit board.

11. The patch-type sensor module of claim 1, wherein an adhesive member is disposed on one surface of the protection member.

12. The patch-type sensor module of claim 1, wherein the protection member is made of a material having flexibility.

13. The patch-type sensor module of claim 1, wherein the patch-type sensor module further includes:
a base substrate having flexibility and air permeability; and
a medicinal solution layer including a functional material disposed on one surface of the base substrate.

14. The patch-type sensor module of claim 13, wherein the base substrate is formed of a nanofiber web of a three-dimensional network structure having micropores.

15. The patch-type sensor module of claim 13, wherein the medicinal solution layer is formed of a nanofiber web accumulated by electrically spinning a spinning solution in which a functional material, a water-soluble polymer, and a solvent are mixed.

16. A patch-type sensor module comprising:
a plate-shaped flexible battery electrically connected to a flexible circuit board so as to provide driving power and disposed in an incised portion formed on one side of the flexible circuit board;
a temperature sensor mounted on one surface of the flexible circuit board to measure a user's body temperature;
a communication unit including a near field communication (NFC) antenna module and a Bluetooth module for allowing power supply using a wake-up function and for transmitting information measured by the temperature sensor to an external communication module through a pairing with the external communication module when power is supplied;
a control unit configured to control driving of the flexible battery, the temperature sensor, and the communication unit; and
a protection member made of a material having flexibility and configured to prevent the flexible circuit board, a power supply unit, the temperature sensor, the communication unit, and the control unit from being exposed to an outside,
wherein the flexible circuit board includes an incised portion having a predetermined area and formed to be incised inward in a thickness of the flexible circuit board; and
the power supply unit is disposed in the incised portion such that all of a thickness of the power supply unit corresponding to a thickness of the flexible circuit board is accommodated by the incised portion,
wherein the power supply unit is disposed in the incised portion and is not stacked on a surface of the flexible circuit board,
wherein the flexible circuit board comprises a pair of electrodes mounted on one surface thereof and configured to be convex to a user's skin, and
wherein the power supply contact pads are electrically connected to the flexible circuit board in the incised portion.

17. A patch-type sensor module comprising:
a power supply unit electrically connected to a flexible circuit board;
a sensing unit mounted on the flexible circuit board and including a temperature sensor configured to measure a user's body temperature;
a communication unit for allowing power to be supplied using a wake-up function and for transmitting information measured by the sensing unit to an external communication module through a pairing with the external communication module when power is supplied;
a control unit configured to control driving of the power supply unit, the sensing unit, and the communication unit; and
a protection member configured to prevent the flexible circuit board, the power supply unit, the sensing unit, the communication unit, and the control unit from being exposed to an outside,
wherein the flexible circuit board includes an incised portion having a predetermined area and formed to be incised inward in a thickness of the flexible circuit board; and
the power supply unit is disposed in the incised portion such that all of a thickness of the power supply unit corresponding to a thickness of the flexible circuit board is accommodated by the incised portion,
wherein the power supply unit is disposed in the incised portion and is not stacked on a surface of the flexible circuit board,
wherein the flexible circuit board comprises a pair of electrodes mounted on one surface thereof and configured to be convex to a user's skin,
wherein the flexible circuit board includes a protection circuit to prevent overcharge during charging of the power supply unit, and
wherein the power supply contact pads are electrically connected to the flexible circuit board in the incised portion.

* * * * *